United States Patent [19]
Honig et al.

[11] Patent Number: 5,638,171
[45] Date of Patent: Jun. 10, 1997

[54] SPECTROPHOTOMETER WITH SELF-CONTAINED MODULE

[76] Inventors: Jordan S. Honig, 6242 Buchanan St., Ft. Collins, Colo. 80525; Robert S. Blythe, 2604 El Rancho Dr., Loveland, Colo. 80538

[21] Appl. No.: 398,458

[22] Filed: Mar. 3, 1995

[51] Int. Cl.⁶ .................................................. G01N 21/01
[52] U.S. Cl. ..................... 356/244; 356/246; 356/410; 356/326
[58] Field of Search .................................. 356/319, 246, 356/244, 410, 326

[56] References Cited

U.S. PATENT DOCUMENTS

| | | | |
|---|---|---|---|
| 3,806,259 | 4/1974 | Boostrom et al. | 356/244 |
| 4,254,084 | 3/1981 | Blum | 356/246 |
| 4,683,120 | 7/1987 | Meserol et al. | 356/246 |
| 4,717,827 | 1/1988 | Harvey | 356/246 |
| 5,204,270 | 4/1993 | LaCount | 356/246 |

*Primary Examiner*—K. Hantis
*Attorney, Agent, or Firm*—Dean P. Edmundson

[57] ABSTRACT

A spectrophotometer which accommodates a self-contained sample module. Sample modules are interchangeable and can be readily inserted into, or removed from, the spectrophotometer without tools. Guides in the spectrophotometer assure that the modules are properly aligned when inserted. The module houses the sample(s) to be tested. Sample cell holders may be removed from the module and replaced with other cell holders. When the module is inserted into the spectrophotometer, optical alignment, mechanical alignment, proper electrical connection and software interface are all achieved in one common installation procedure for all sample modules.

21 Claims, 14 Drawing Sheets

SPECTROPHOTOMETER WITH SELF-CONTAINED MODULE

FIELD OF THE INVENTION

This invention relates to spectrophotometers. More particularly, this invention relates to spectrophotometers and sample handling techniques and apparatus.

BACKGROUND OF THE INVENTION

Spectrophotometers are conventional laboratory instruments which are used for analyzing liquid samples by transmitting a light beam of known wavelength and intensity through the sample. This is important in tests such as colorimetry, fluorolumenescence, and turbidimetry.

The amount of light absorbed, transmitted, reflected or emitted by the sample is instructive of the physical properties and the concentrations of the sample's chemical components.

In a typical spectrophotometer, a liquid sample is placed in a special sample cell which has walls of transparent material (such as glass). The sample cell is then inserted into a sample cell receiver or holder in the spectrophotometer, after which a light beam is directed through the sample cell. The amount of light absorbed by the sample can be correlated to the concentration of a particular or selected chemical species in the sample. In order to conduct an analysis of another liquid sample, it is necessary to remove the first sample and insert the new sample.

There have previously been used certain spectrophotometers commercialized which include or utilize multiple sample cells. For example, U.S. Pat. No. 5,059,025 describes a movable sample cell holder which can hold several sample cells. The linear holder is moved laterally in order to position successive sample cells in the light beam so that a reading can be taken for each sample cell.

Linear sample positioners require a compartment length at least twice that of the linear sample cell holding cassette. This tends to limit the number and size of samples or increases the footprint of the sample compartment. Row by column designs add more samples at the expense of increased mechanical complexity.

Linear cartridges may become difficult to handle without touching optical faces of the sample cells and tend to be easily tipped over when laid on the work area due to their long, narrow design. Handling is further comprised since samples are packed close together to optimize use of available length.

Cell holders are generally made of metallic materials which are heavy, sensitive to chemical attack, easily bent and misaligned during handling. Sample holders for test tubes are often avoided due to the optical distortion problems created by the test tubes' lens effect.

Prior art adapters are generally designed as modifications to standard instruments. As such they are delicate and unprotected mechanisms when removed from the instrument enclosure, with the expectation that there will be few instances of replacement with different modifying elements. Testing samples in other formats is thus discouraged due to the time and skill required to change and replace sample adapters.

Previously available spectrophotometers which involve more than one sample module require additional tools, instructions or skills in order to replace one module with another, and they may require further manipulation of the hardware, software, mechanical or electrical connections in order to make these changes. This is cumbersome. Unused modules must be stored in protective boxes, cabinets or containers to protect them from dust, spills, breakage, etc. Also, assembly and disassembly exposes sensitive components to misalignment, lost hardware, fouled connectors, fingerprints on optics, etc. Further optical alignment, software and/or mechanical set up and/or calibration procedures are frequently required before sampling can begin.

There has not heretofore been provided a spectrophotometer having the features and advantages provided by the present invention.

SUMMARY OF THE INVENTION

In accordance with the present invention there is provided an improved spectrophotometer which accommodates a self-contained sample module which enhances the ease and precision with which the instrument can be converted from one sampling format to another format. Unused modules can be easily handled and require no special storage procedures.

The sample modules are interchangeable and can be readily inserted into, or removed from, the spectrophotometer. Guides in the spectrophotometer assure that the modules are properly aligned and positioned when inserted into the spectrophotometer. The modules protect the sample cell(s) from shock, spillage and breakage.

When the sample module is inserted into the spectrophotometer, all electronic connections are automatically updated. All optical and mechanical alignments are also automatically made when the module is installed and locked in place. Installation can be completed without tools and do not require any special skills or knowledge. The software interface is automatically updated when the module is inserted to assure proper use of the module.

Sample cell holders may be removed from the module and replaced with other cell holders without the use of tools. The cells in all cell holders are self aligning and secured by means of plastic holding springs and require no tools for installation. All materials used are durable and chemically resistant.

The modules are composed of chemically-resistant, shock-resistant, optically-opaque plastics. A hinged lid on the module is opaque (to prevent light from entering the module when the lid is in its closed position). The lid may be pivoted to an open position to enable the operator to remove or insert sample cells, replace the pump tube, etc.

Thus, when the module is inserted into the spectrophotometer, optical alignment, mechanical alignment, proper electrical connection and software interface are all achieved in one common installation procedure for all sampling modules. A simple but effective latch mechanism secures the installed module and assures that the proper contacts and alignment will be maintained.

Because the modules of the invention are self-contained and require no assembly tools, manuals or alignment fixtures, idle modules may be stored in a convenient area in the open laboratory. Impact resistant materials and a chemical resistant interior help the units withstand accidental bumps and spills.

Using the modules, tests may be run as single point or as time course experiments. This accommodates both set point and kinetic testing. Also, samples of any material phase, i.e., gas, liquid or solid may be accommodated in the module described herein.

A plurality of individual self-contained modules may be used with a single spectrophotometer. For example, several different laboratories may each have their own module and share a single spectrophotometer base unit. It is also possible to use a separate module for different types of samples. It is further possible to use one module for a single cell, another for a carousel sample holder, and another module for a flow through cell, for example.

Other advantages of the spectrophotometer and the module will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

In the drawings there is shown a spectrophotometer system 10 which includes a removable, self-contained sample module 20. The sample module comprises an enclosure with a hinged lid 22. Samples of liquid to be analyzed in the spectrophotometer are placed in the sample module (e.g., the samples may be contained in vials and placed in a carousel to be positioned in the module, or the module may include a flow cell through which a liquid sample may flow).

The module includes openings 20A in opposite side walls 21 to enable a light beam to pass through the module and the sample, when the module is inserted in the opening 10A in the spectrophotometer 10. Rails or ribs 23 on opposite sides on the module slide between guides 11 and 12 along the side walls of opening 10A in the spectrophotometer so as to properly position the module in the spectrophotometer. Spring chocks 23A fix the module placement once the module has been fully inserted into the instrument.

With this arrangement, the sample to be tested remains inside the module and minimizes handling of the sample. Also, several samples can be placed in a carousel which is then positioned in the module where the samples can be tested individually when the carousel is rotated from one position to another, as will be explained in more detail hereinafter.

Figure 1:
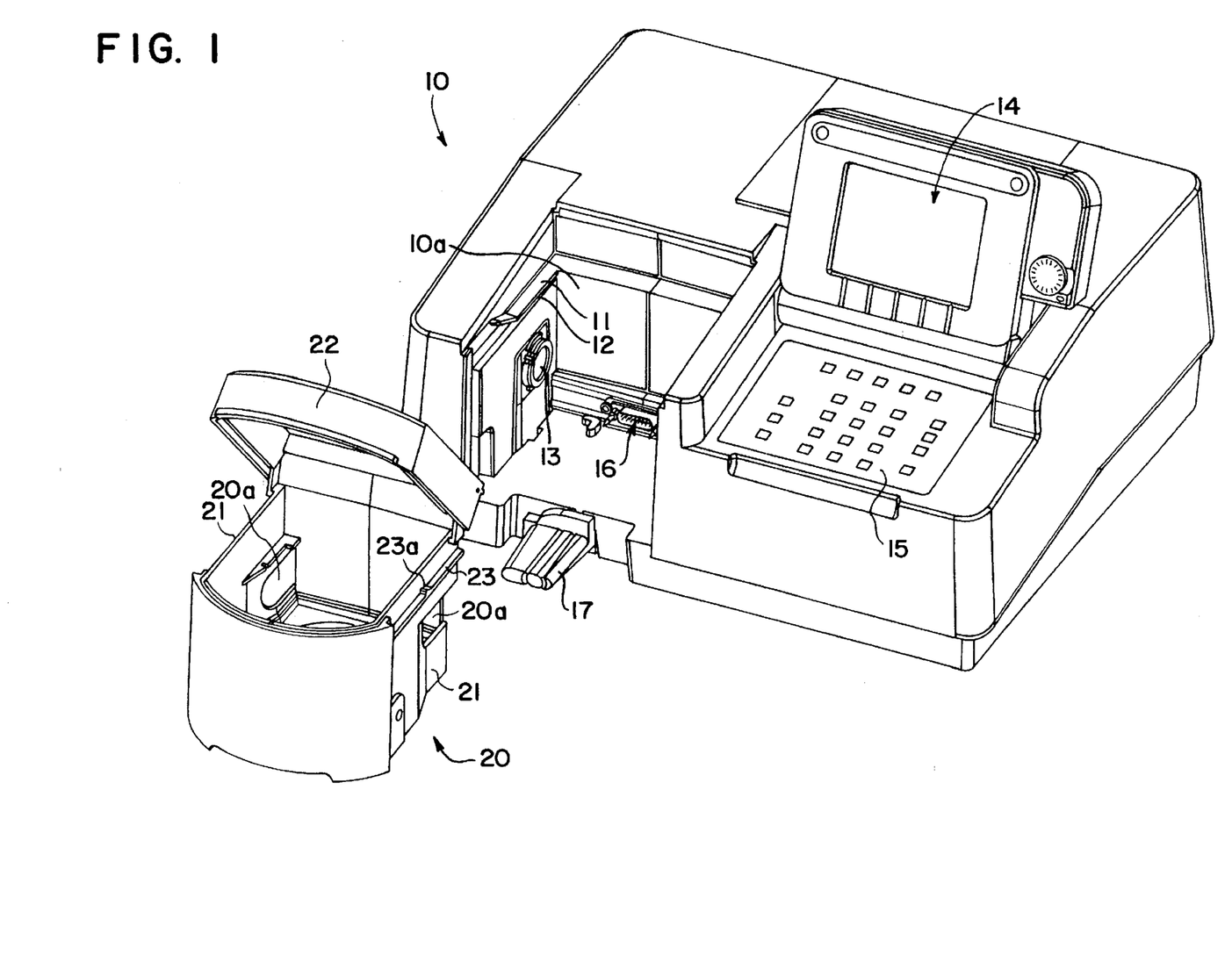
FIG. 1 is a perspective view of one embodiment of spectrophotometer and sample module of the invention.
Figure 2:
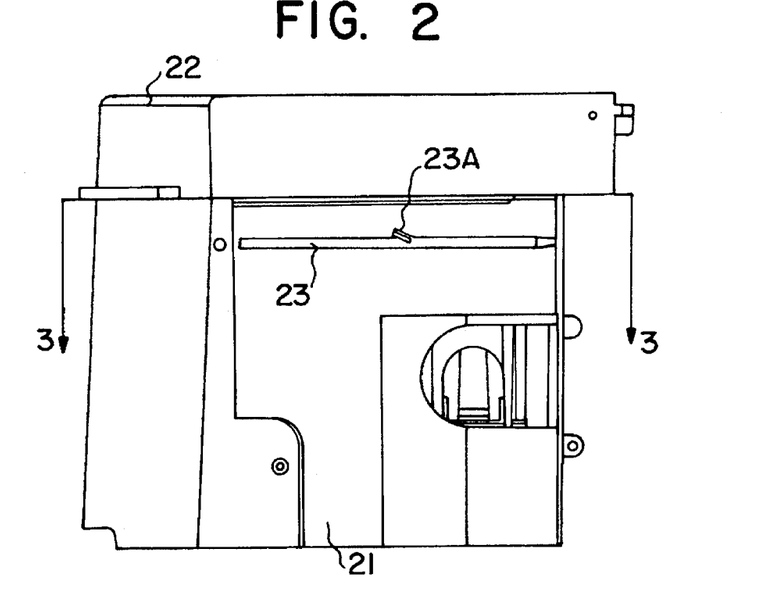
FIG. 2 is a side elevational view of the module shown in FIG. 1.

The spectrophotometer 10 includes an optical display screen 14 which is hinged to the housing of the spectrophotometer and can be pivoted between a raised position (shown in FIG. 1) and a lowered position where it covers the operator keypad 15. The spectrophotometer also includes a light source, mirrors, and appropriate light detector 13 for measuring the amount of light transmittance through a sample cell. The light path in the instrument is shown in dotted lines in FIG. 26.

The spectrophotometer further includes an electrical connector 16 in the opening 10A for establishing an electrical connection with a mating connector 26 in the module 20 when the module is positioned in the opening. Latch 17 is pivotable between locked and unlocked positions. When in the unlocked position (shown in FIG. 1), it is possible to insert or remove the module. When in the locked position, the latch secures the module in the instrument.

The electrical connection between the module and the instrument serves to identify the type of module configuration that has been loaded into the instrument. This enables the instrument to set up the appropriate screen with user-selectable parameters. Also, the electrical connector has a self-alignment feature that assures reliable, repeatable electrical connections from any module to any instrument.

The electrical connector is further used to supply power to active components in the module, such as motors, to send signal information from sensors in the module to the instrument computer regarding cell position in the module, ambient light and other critical parameters from the sample area.

Figure 3:
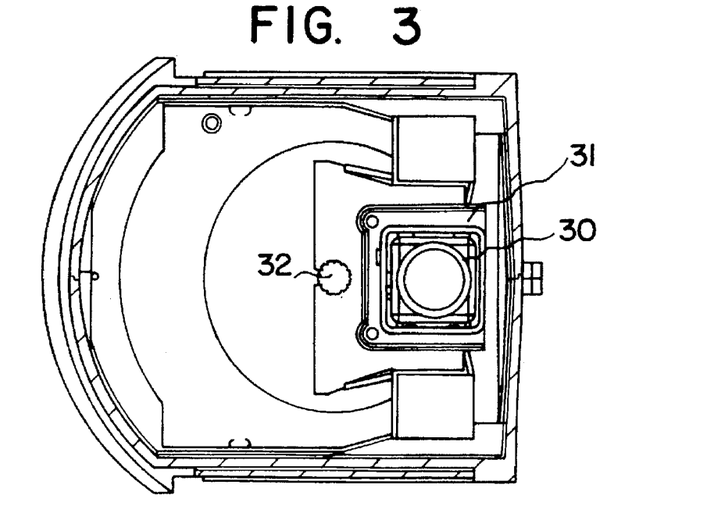
FIG. 3 is a sectional view of the sample module shown in FIG. 2 taken along line 3—3.
Figure 4:
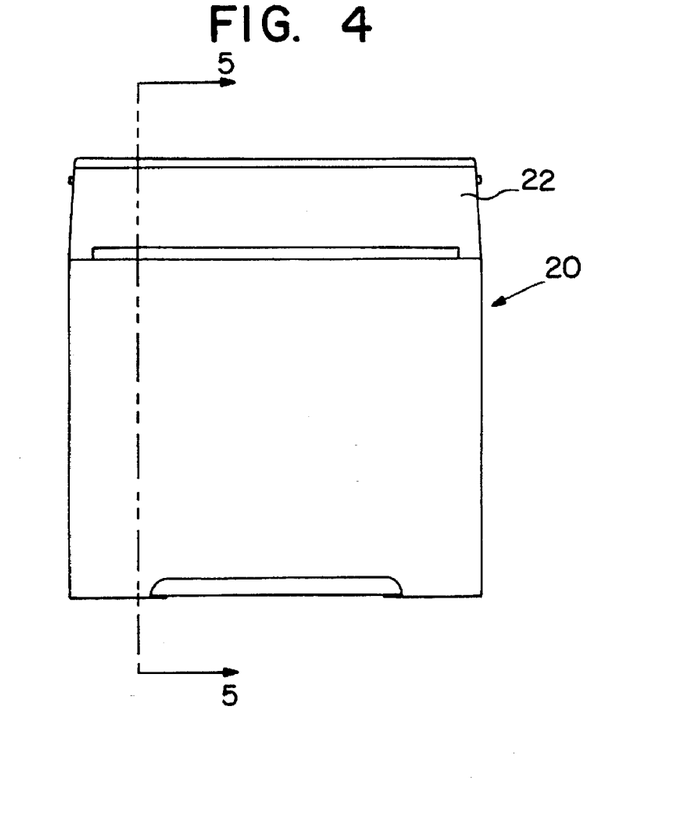
FIG. 4 is a front elevational view of the sample module.
Figure 5:
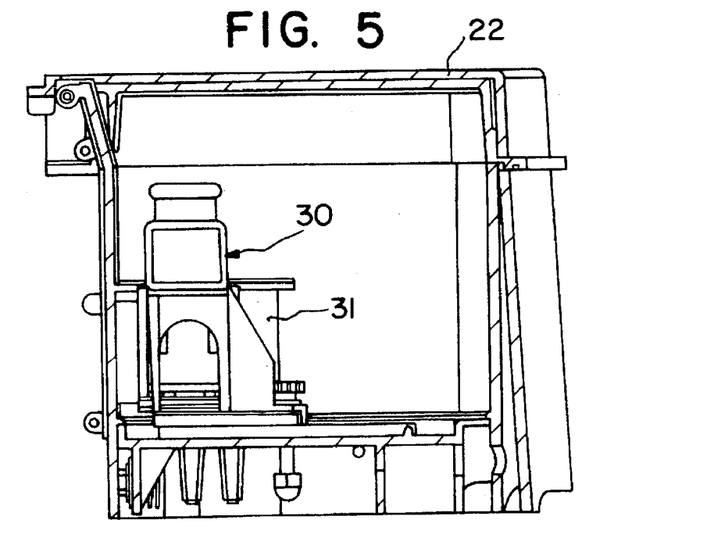
FIG. 5 is a sectional view of the module taken along line 5—5 in FIG. 4.
Figure 6:
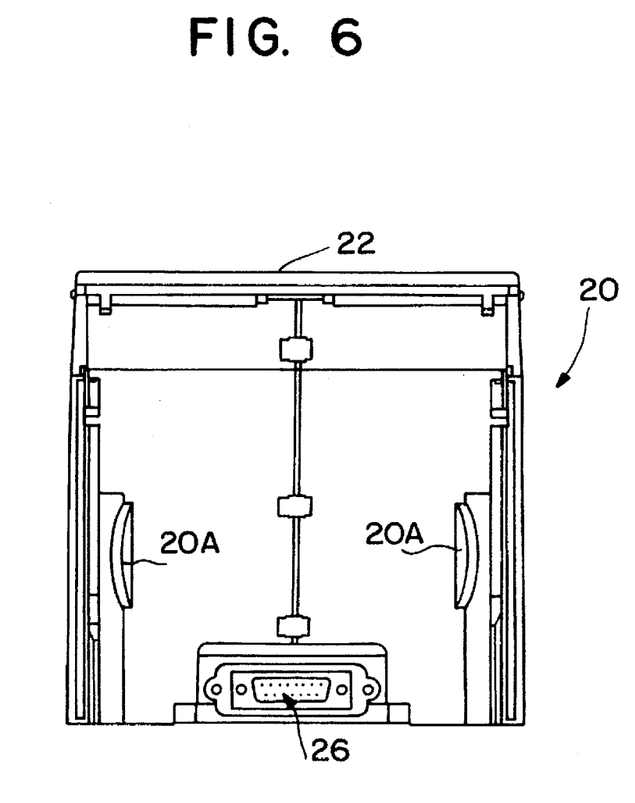
FIG. 6 is a rear elevational view of the sample module.
Figure 7:
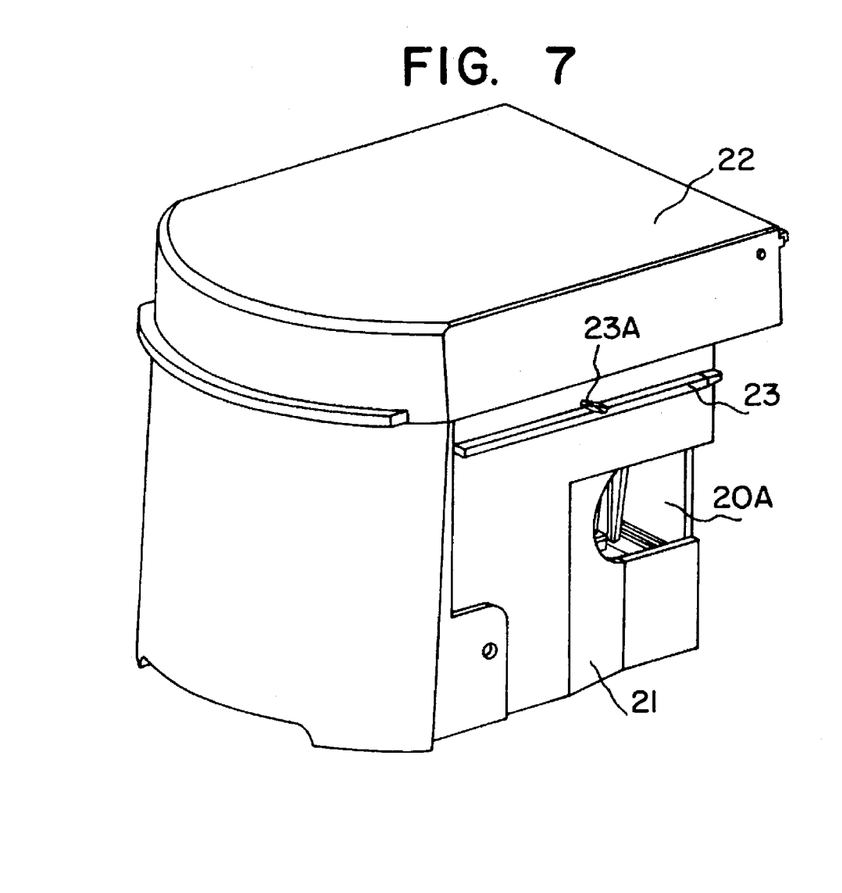
FIG. 7 is a front perspective view of the sample module.
Figure 8:
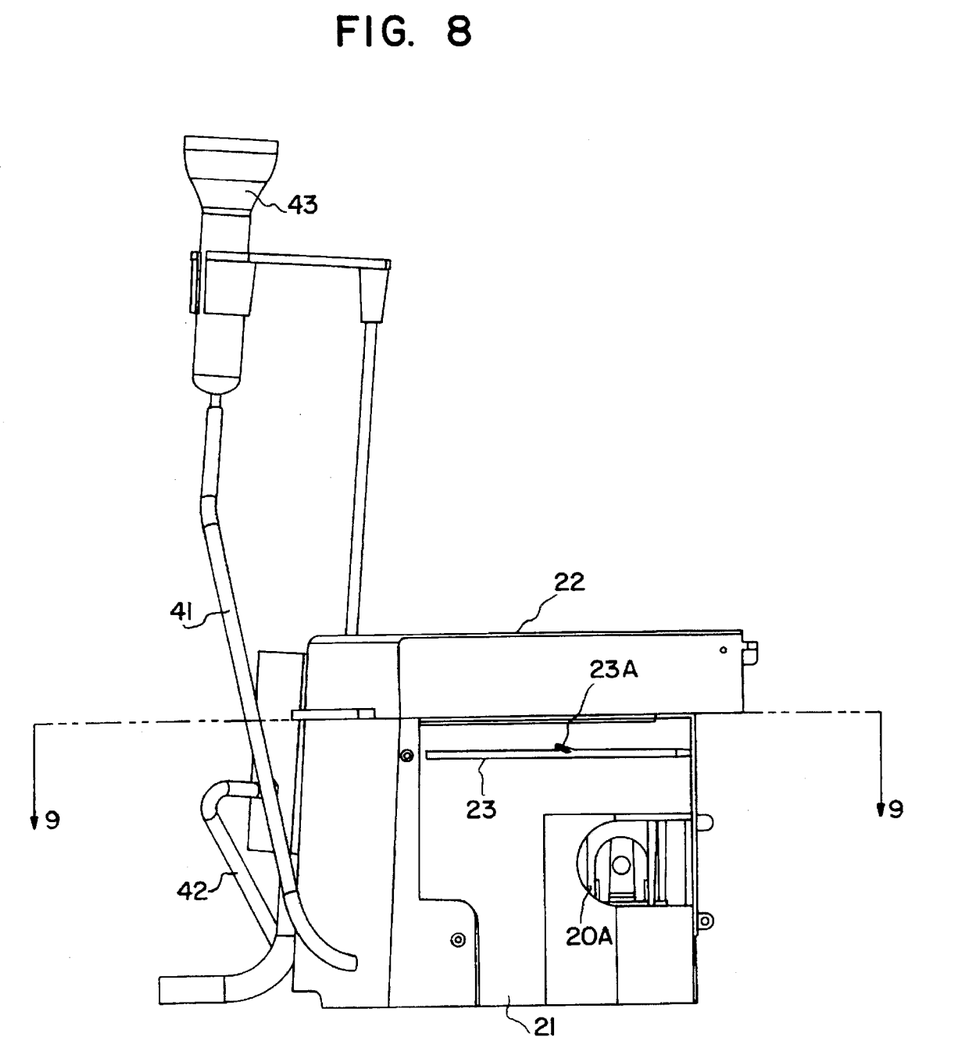
FIG. 8 is a side elevational view of another embodiment of sample module.
Figure 9:
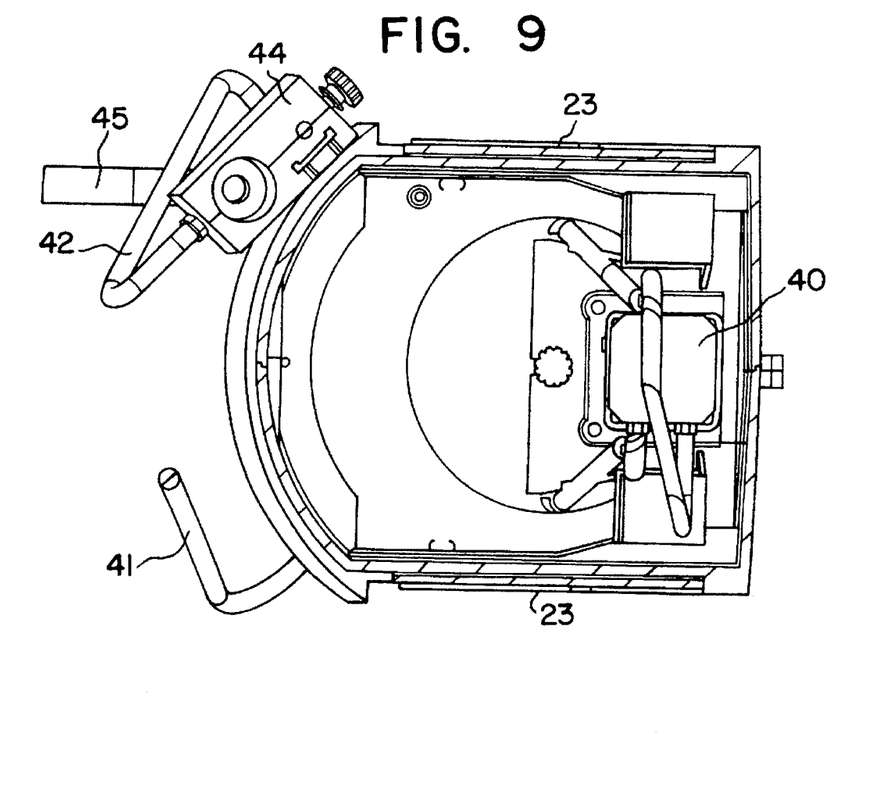
FIG. 9 is a sectional view of the module shown in FIG. 8 taken along line 9—9.
Figure 10:
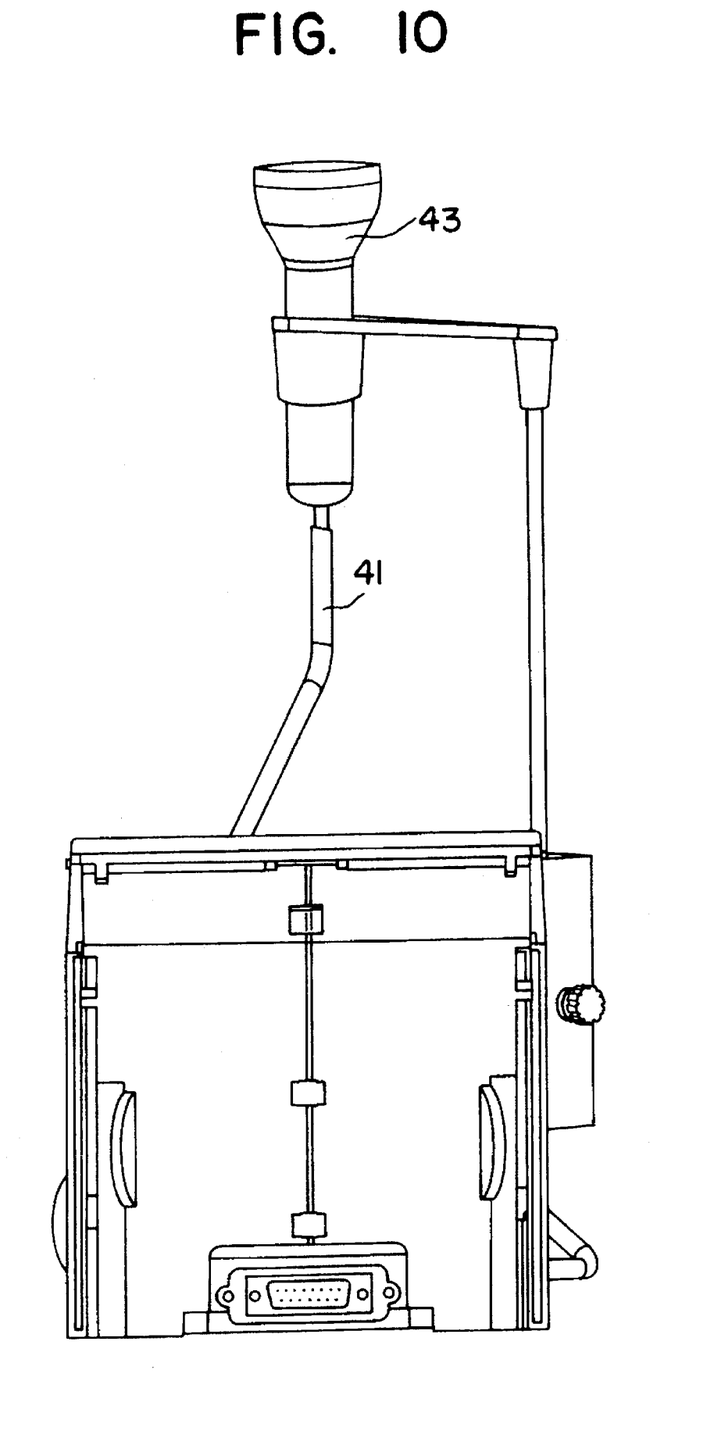
FIG. 10 is a rear elevational view of the sample module shown in FIG. 8.
Figure 11:
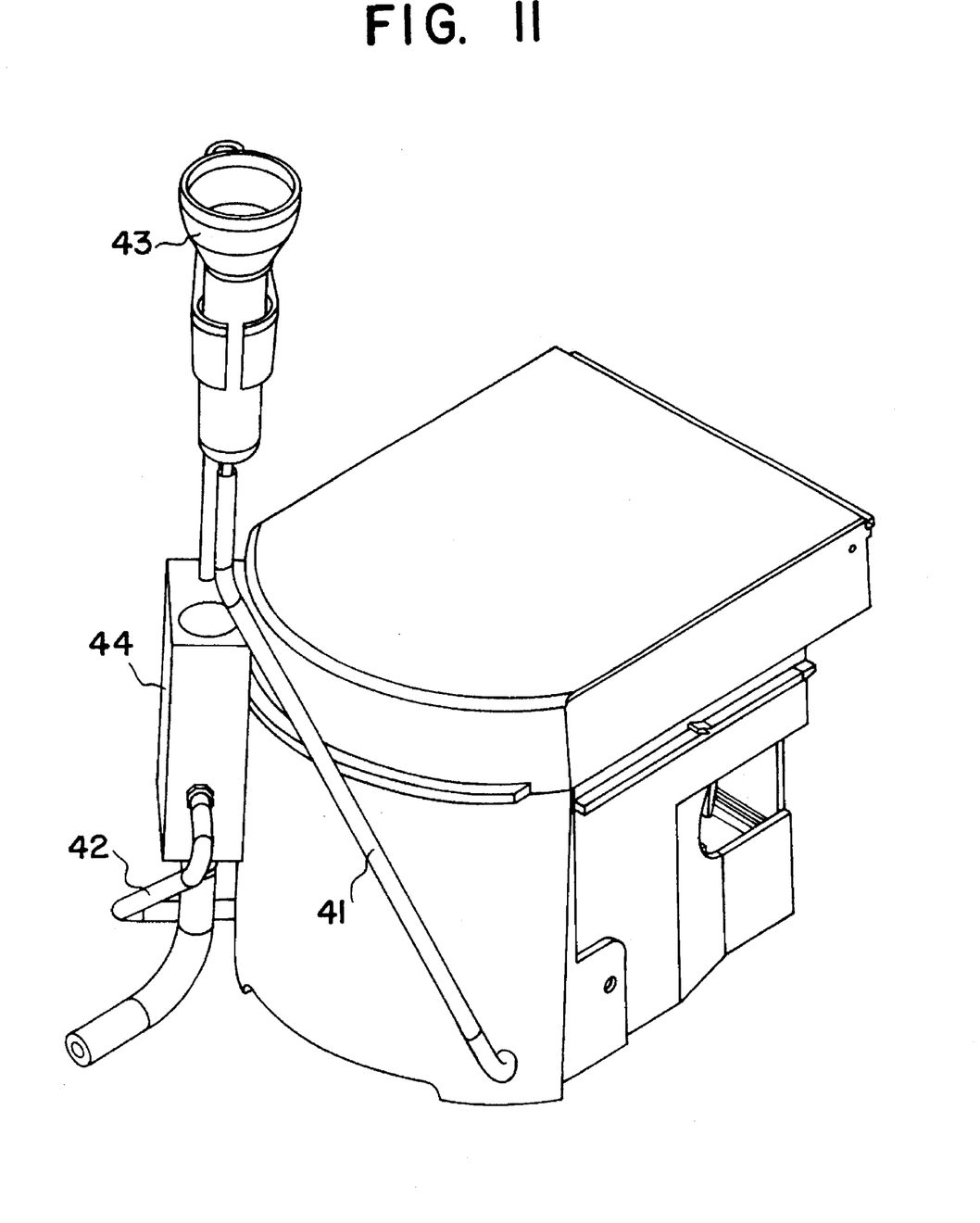
FIG. 11 is a front perspective view of the sample module shown in FIG. 8.
Figure 12:
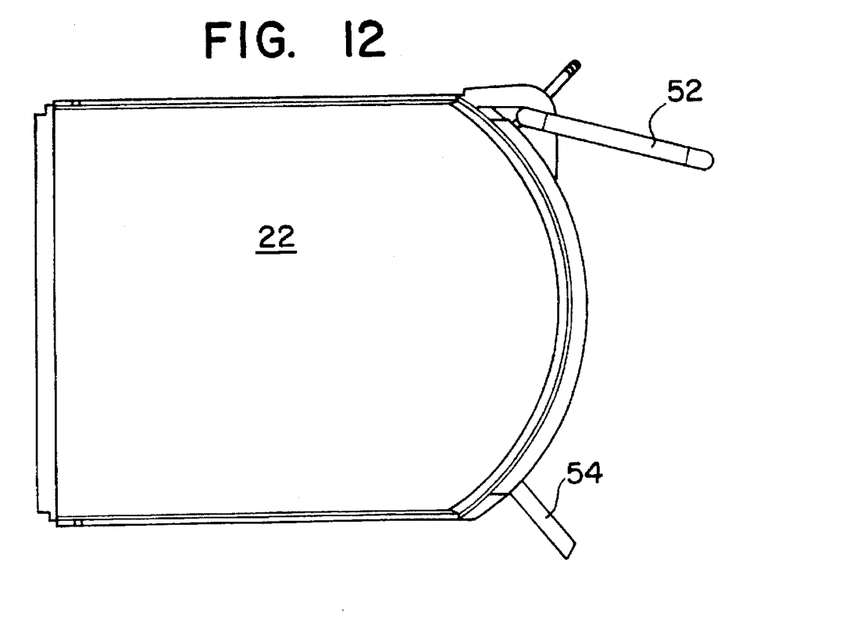
FIG. 12 is a top view of another embodiment of sample module useful in this invention.
Figure 13:
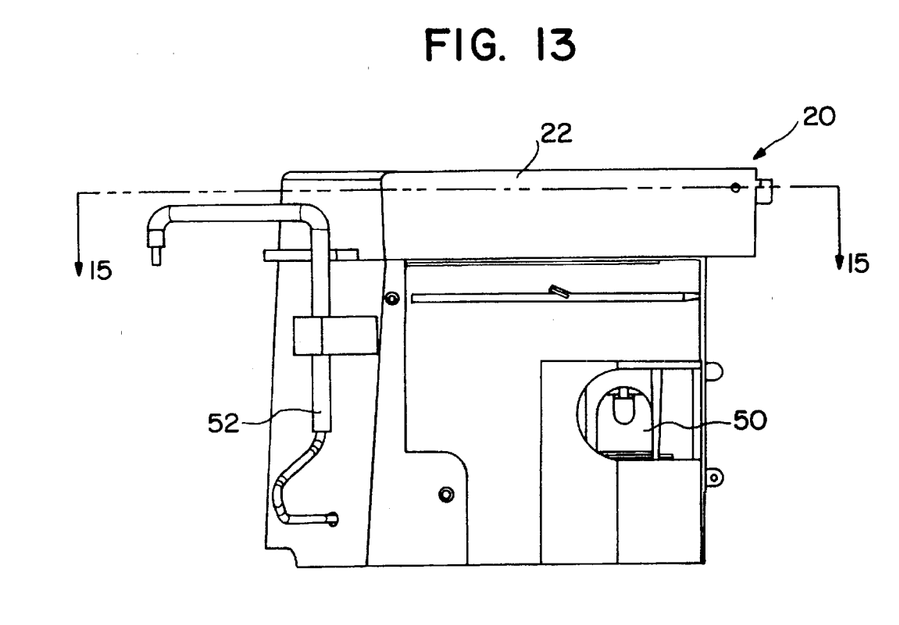
FIG. 13 is a side elevational view of the sample module shown in FIG. 12.
Figure 14:
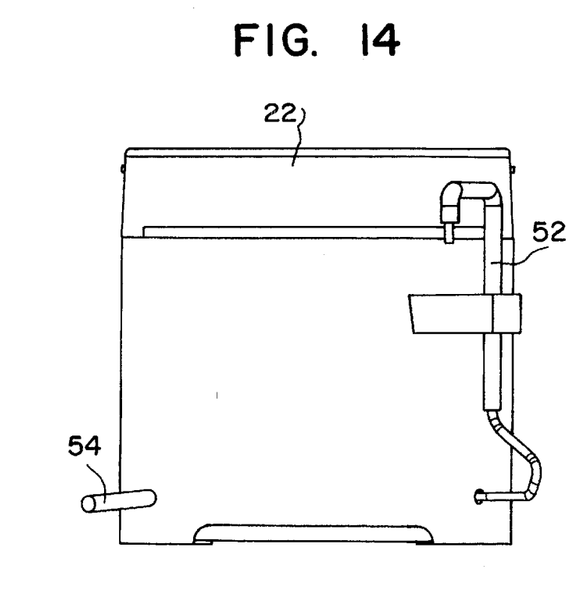
FIG. 14 is a front elevational view of the sample module shown in FIG. 12.
Figure 15:
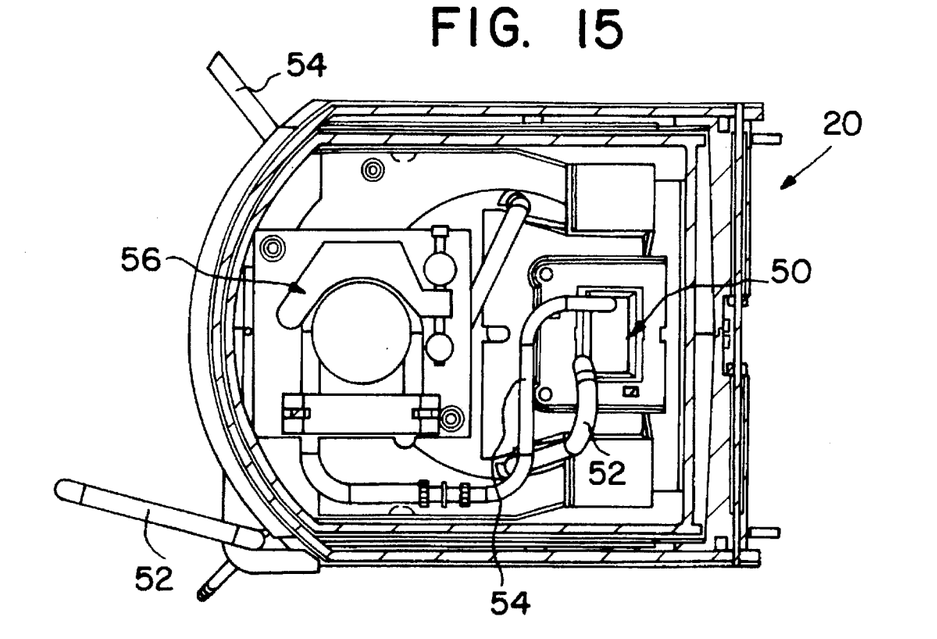
FIG. 15 is a sectional view of the module shown in FIG. 13 taken along line 15—15.
Figure 16:
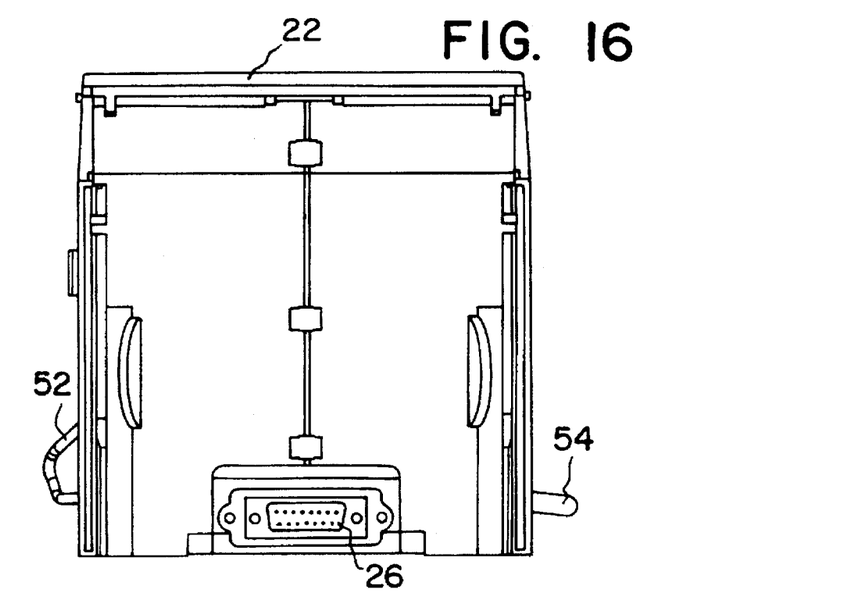
FIG. 16 is a rear elevational view of the module shown in FIG. 12.

FIGS. 3 and 5 are cross-sectional views of the module showing a single sample cell 30 positioned in the module in a cell holder 31. Screw 32 secures the holder in the module.

FIGS. 8–11 show another embodiment of module 20 which has been fitted with a flow through sample cell 40 positioned between the two openings 20A in the side walls 21 of the module. Tube 41 is connected between funnel 43 and sample cell 40. Tube 42 leads from the sample cell to a vacuum break base 44 which controls the rate of flow of the liquid sample through the cell 40. The sample eventually exits the system through outlet tube 45. This arrangement enables a desired liquid sample to be tested in the spectrophotometer without the need for handling the sample cell. After one sample has been tested, another sample can be tested in the same manner without having to remove the sample cell or the module.

This embodiment allows for rinsing the sample cell between tests, thus reducing contamination from previous samples. Since the cell does not move between tests, sample comparisons can be made without any variable of sample position. Furthermore, the likelihood of fingerprints, smudges, dirt, etc. on the optical faces is reduced. Due to the ease of system operation, this configuration lends itself to repetitive testing with little handle, and is suited for automated tests.

FIGS. 12–16 show another embodiment of module of this invention which has been fitted with a sipper sample cell 50. An inlet tube 52 leads from a liquid sample source to the sample cell 50. Outlet tube 54 leads from the outlet end of the sample cell, through peristaltic pump 56, and out through the front of the module 20. Operation of the pump draws liquid sample through the sample cell and then out through the outlet tube 54. While the sample is passing through the sample cell, various desired measurements may be taken with the instrument.

This embodiment pulls sample through the cell via a pump mechanism. Sample volume, settling time, and flush volume are controlled as user input parameters. The pumping rate may be controlled by changing the roller compression on the pump tubing, or replacing the pump tubing with one of a different diameter.

Figure 17:
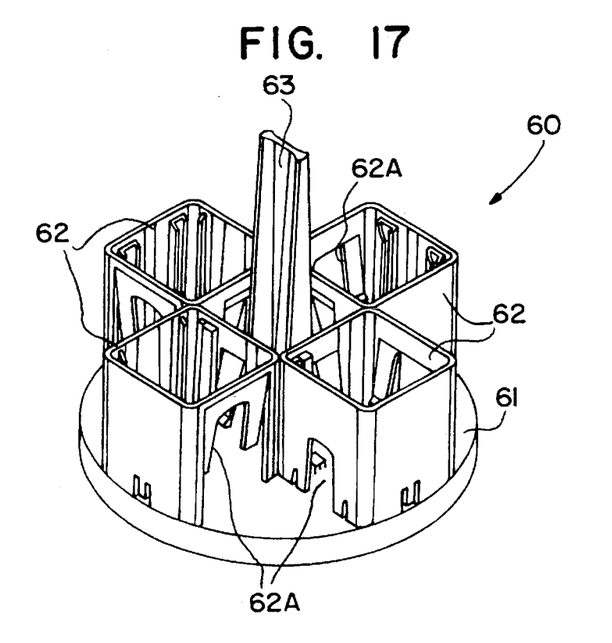
FIG. 17 is a perspective view of one embodiment of sample holder.
Figure 18:
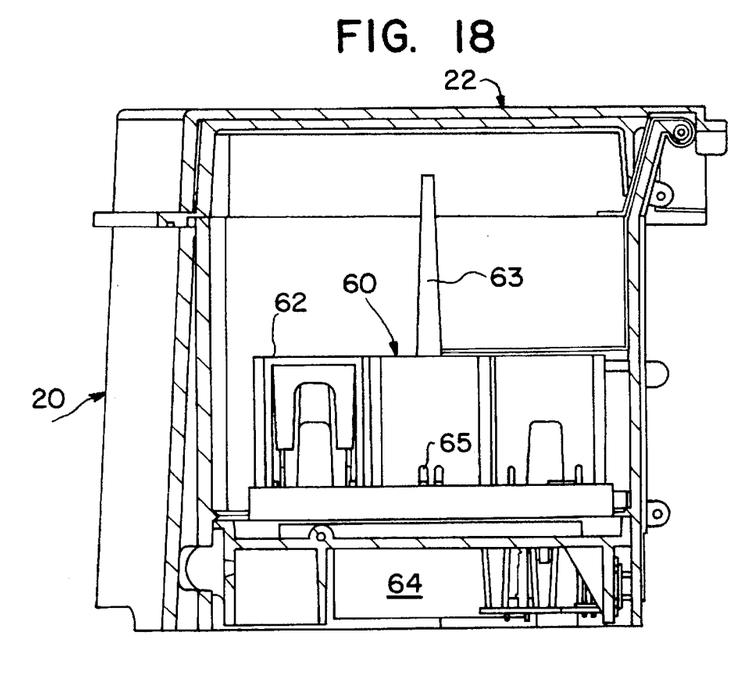
FIG. 18 is a cross-sectional view of the sample module with the sample holder of FIG. 17 therein.
Figure 25:
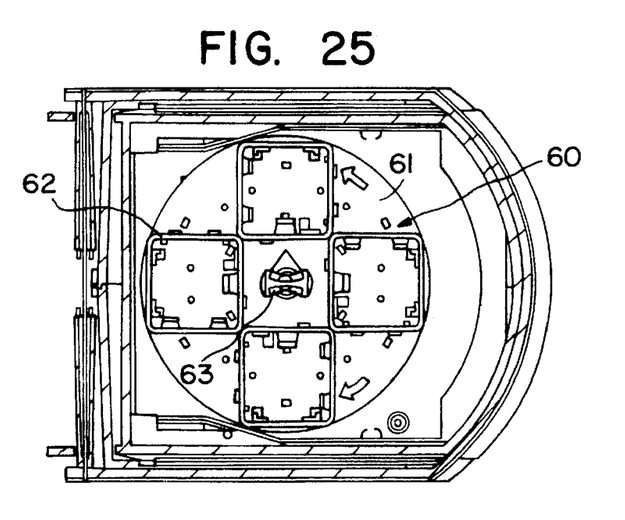
FIG. 25 is a top view of the sample module with a carousel positioned in the module.

FIGS. 17, 18 and 25 show one embodiment of a carousel sample cell holder 60 comprising a generally disk-shaped base portion 61 which supports four equidistantly spaced sample cell holders or compartments 62. Stem or handle 63 projects upwardly from the center of the carousel to a point above the height of the sample cell compartments. The handle is useful in handling and carrying the carousel with sample cells in the compartments. The handle is also used when placing the carousel into the module 20 and also when removing the carousel from the module.

Each compartment 62 include openings 62A in opposite side walls thereof (as illustrated in the drawings). The openings 62A in each compartment enable the light beam in the spectrophotometer to pass through a sample cell contained in the compartment.

After a measurement has been taken on a liquid sample in a sample cell in one compartment, the carousel can be rotated 90° so as to position the next compartment in the path of the light beam. Then a measurement can be taken on the sample present in such compartment. This procedure can be repeated until the samples in all of the compartments in the carousel have been tested.

Rotation of the carousel from one station to the next is effected by means of electric motor 64 located in the base of the module 20. The motor is operatively connected to electric power by means of the mating electrical connectors 26 and 16. The operation of the motor is controlled by user interface programs indicating reference and sample requirements. Motor 64 drives a vertical shaft 64 in the base of the module. The carousel base can be connected or locked to the shaft so that the carousel will be rotated by the motor shaft. Magnets placed or secured on the bottom of the carousel are used to determine the rotational position of the carousel in the module.

Figure 19:
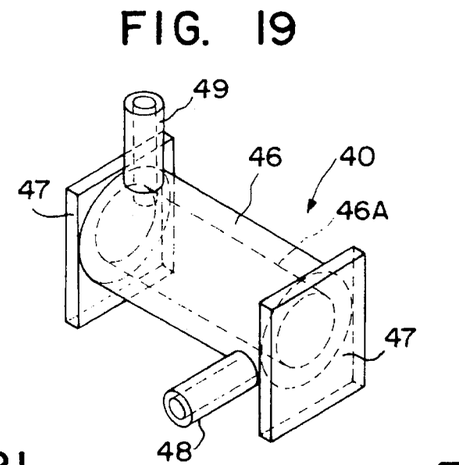
FIG. 19 is a perspective view of a preferred embodiment of flow cell which is useful in the present invention.
Figure 20:
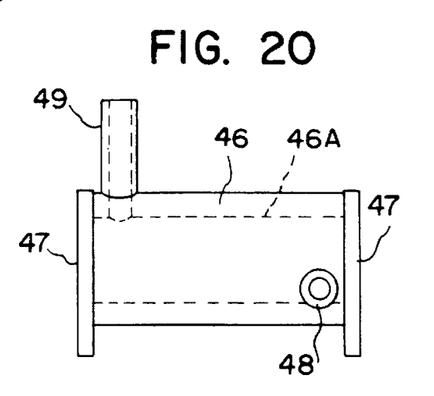
FIG. 20 is a front elevational view of the flow cell shown in FIG. 19.
Figure 21:
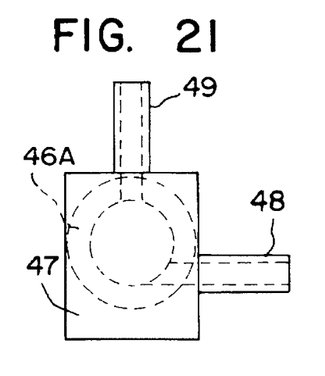
FIG. 21 is an end elevational view of the flow cell shown in FIG. 19.

FIGS. 19–21 show a preferred embodiment of flow cell 40 which can be used in the module in accordance with this invention. The flow cell comprises a cylindrical body 46 having parallel end walls 47 which are preferably perpendicular to the longitudinal centerline of the cylindrical body 46. The end walls are optically clear and transparent to enable the light beam to pass through the end walls and longitudinally through the cavity 46A in the body 46.

The inlet 48 into the cavity in the body 46 is located near one end of the body and is tangential to the bottom of the cylindrical cavity, as shown in the drawings. The centerline of the inlet tube is parallel to the end wall 47. The outlet 49 from the cavity is located at the top of the body 46 and is perpendicular to the centerline of the cavity 46A. It is positioned near the end of the body opposite from the location of the inlet.

With the arrangement of the inlet and outlet tubes as shown herein, the liquid sample is caused to swirl in a helical path as it passes through the body 46. This action keeps the interior surface of the cavity 46A flushed clean with a minimum volume of fluid and thereby prevents deposits or scum from forming on the interior surfaces. With the outlet tube being located at the top of body 46, air bubbles are able to easily and readily exit the body 46 through the outlet tube. In this manner, air bubbles do not accumulate in the body where they could interfere with making measurements.

Figure 22:
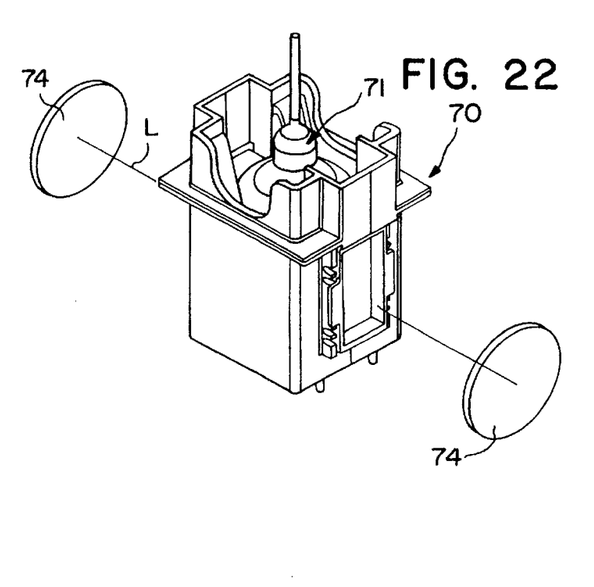
FIG. 22 is a perspective view of a preferred embodiment of sample cell holder for use in this invention.
Figure 23:
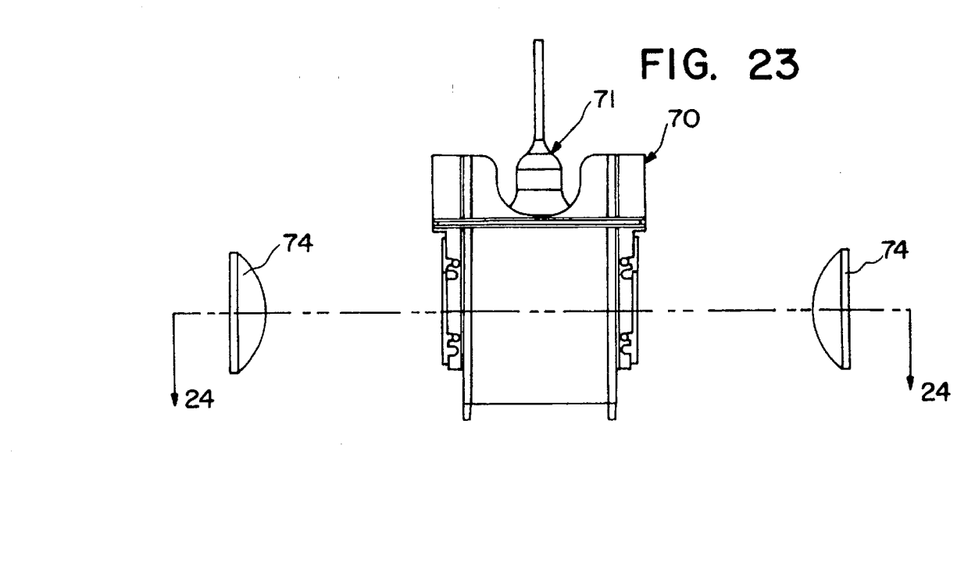
FIG. 23 is a front elevational view of the cell holder shown in FIG. 22.
Figure 24:
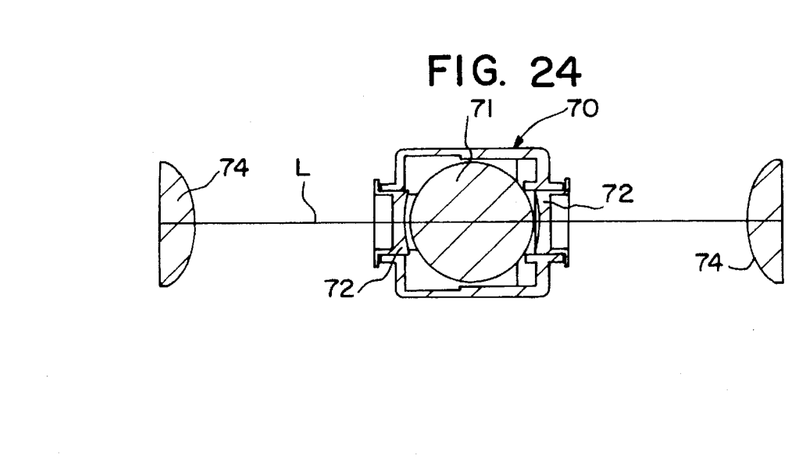
FIG. 24 is a cross-sectional view of the cell holder shown in FIG. 23 taken along line 24—24.

FIGS. 22–24 illustrate another embodiment of sample cell holder 70 which is adapted to hold a cylindrical sample cell 71. The holder includes a plano-concave lens 72 on opposite sides of the sample cell. The side of each lens adjacent the sample cell has a curvature which compensates for distortion due to light passing through the cylindrical sample cell. Thus, a light beam L directed at the sample cell passes through a plano-convex lens 74, straight through the holder and the cell without bending or scattering, and finally through plano-convex lens 74 on the other side of the cell.

Figure 26:
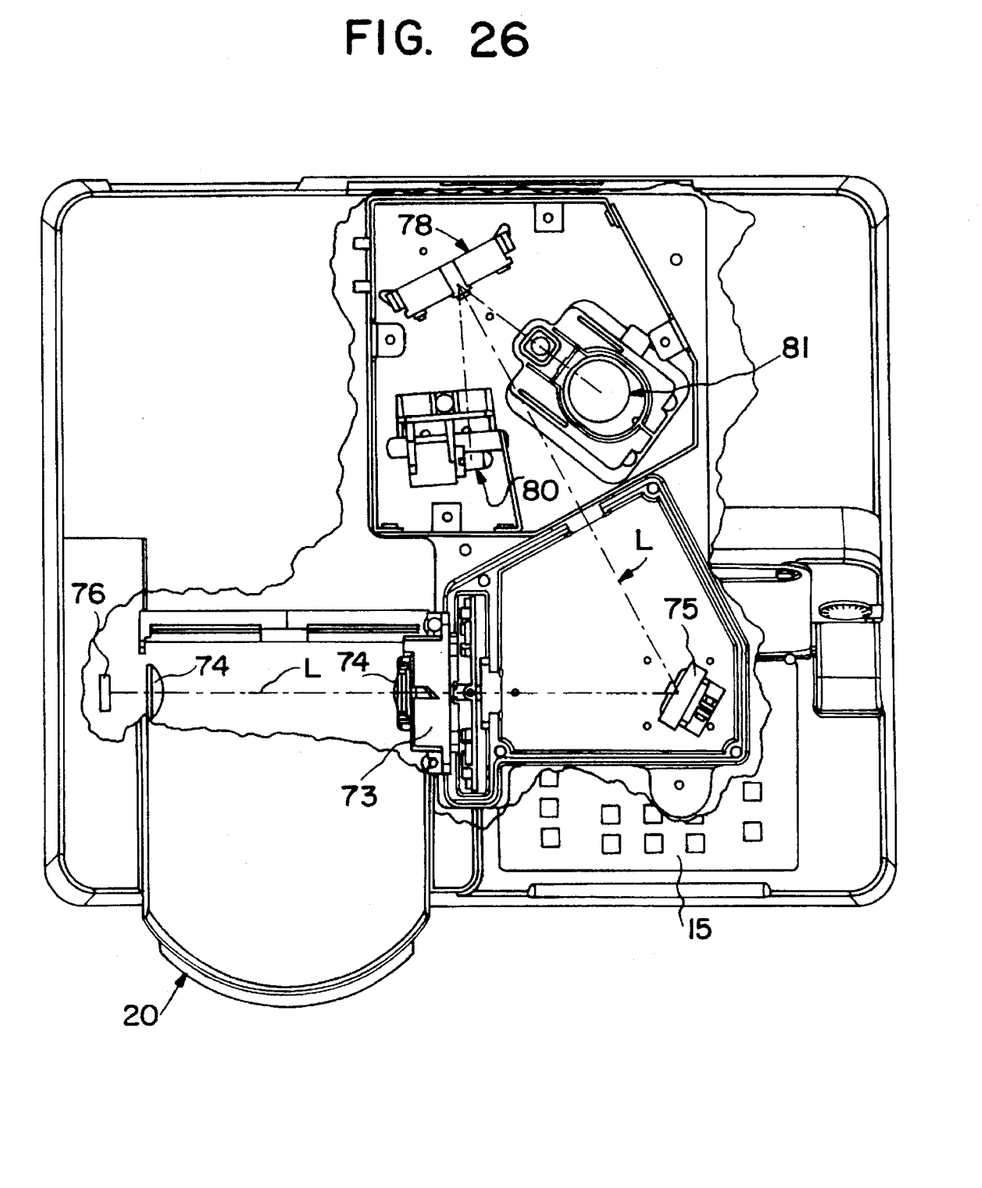
FIG. 26 is a top view of the spectrophotometer showing the optical system and light path in the instrument.

FIG. 26 is a top view, partially cut-away, of the spectrophotometer showing the optical system and the light path. A light beam may be provided by a tungsten lamp 80 (for light having a wavelength in the range of 320 to 1100 nm) or deuterium lamp 81 (for light having a wavelength in the range of 190 to 320 nm). Spherical mirror assembly 78 directs the light beam (from either lamp) to a holographic grating assembly 75, after which the light beam passes through a reference detector assembly 73, then through the first lens 74, the sample to be tested, and the second lens 74. Then the light is detected by measurement detector 76, as shown. The reference detector assembly includes a beam-splitter for sending a portion of the light beam to a silicon photodiode (for the purpose of monitoring the stability of the light beam being introduced into the sample area).

Other variants are possible without departing from the scope of this invention.

What is claimed is:

1. A spectrophotometer of the type including a light source and light detection means, wherein the improvement comprises a removable module for holding a sample to be tested; wherein said spectrophotometer includes a receiving port for receiving said module; wherein said module comprises an enclosure with lid means movable between open and closed positions; and wherein said module enclosure includes opposing side walls having openings for a light beam from said light source to pass through said module; wherein said module and said spectrophotometer further comprise mating electrical connectors; wherein electrical connections are established when said module is inserted into said receiving port in said spectrophotometer.

2. A spectrophotometer in accordance with claim 1, wherein said spectrophotometer further comprises latch means for locking said module in said spectrophotometer.

3. A spectrophotometer in accordance with claim 1, wherein said module enclosure further comprises rail means on opposite sides of said enclosure; and wherein said spectrophotometer includes spaced-apart tracks for receiving and guiding said rail means on said module enclosure.

4. A spectrophotometer in accordance with claim 1, wherein said module further comprises a sample cell holder detachably mounted therein.

5. A spectrophotometer in accordance with claim 1, wherein said module further comprises a flow-through sample cell, wherein said cell includes an inlet and an outlet.

6. A spectrophotometer in accordance with claim 5, further comprising an inlet tube connected to said inlet and a peristaltic pump operably connected to said inlet tube for forcing a fluid sample through said inlet tube into said sample cell.

7. A spectrophotometer in accordance with claim 5, further comprising an inlet tube connected to said inlet and a funnel connected to said inlet tube.

8. A spectrophotometer in accordance with claim 7, further comprising an outlet tube connected to said outlet.

9. A spectrophotometer in accordance with claim 4, wherein said sample cell holder comprises a carousel having a base and a plurality of compartments supported by said base for receiving a plurality of sample cells; wherein said module further includes a motor for rotating said carousel.

10. A spectrophotometer in accordance with claim 9, wherein said module enclosure includes opposing side walls; wherein one said opening is located in each said side wall; and wherein said sample compartments are sequentially positioned between said openings in said opposing side walls.

11. In combination, (a) a spectrophotometer of the type including a light source and light detection means, and (b) a module for holding a sample to be tested; wherein said module comprises an enclosure with lid means movable between open and closed positions; and wherein said module enclosure includes openings for a light beam from said light source to pass through said module; wherein said spectrophotometer includes a receiving port for receiving said module and optically aligning said module between said light source and said detection means, wherein said spectrophotometer further includes latch means for locking said module in said receiving port; and wherein said module and said spectrophotometer further comprise mating electrical connectors.

12. A module for holding and supporting a sample to be tested in a spectrophotometer of the type including a receiving port for receiving said module; wherein said module comprises an enclosure with lid means movable between open and closed positions; wherein said module enclosure includes openings enabling a light beam to pass therethrough; wherein said module enclosure includes opposing side walls, and wherein one said opening is located in each said side wall; wherein said module enclosure further comprises rail means on opposite sides thereof for enabling said enclosure to be guided into said receiving port and positioning said enclosure therein; and wherein said module further comprises a sample cell holder detachably mounted therein; and wherein said module further comprises an electrical connection port for enabling electrical connection between said module and said spectrophotometer when said module is inserted into said receiving port in said spectrophotometer.

13. A module in accordance with claim 12, wherein said module further comprises a flow-through sample cell, wherein said cell includes an inlet and an outlet.

14. A module in accordance with claim 13, further comprising an inlet tube connected to said inlet and a peristaltic pump operably connected to said inlet tube for forcing a fluid sample through said inlet tube into said sample cell.

15. A module in accordance with claim 13, further comprising an inlet tube connected to said inlet and a funnel connected to said inlet tube.

16. A module in accordance with claim 15, further comprising an outlet tube connected to said outlet.

17. A module in accordance with claim 12, wherein said sample cell holder comprises a carousel having a base and a plurality of compartments supported by said base for receiving a plurality of sample cells; wherein said module further includes a motor for rotating said carousel.

18. A module in accordance with claim 12, wherein said sample cell holder comprises a carousel rotatably mounted on a shaft, and further comprising magnets secured to said carousel for identifying the rotational position of said carousel.

19. A flow cell useful for containing a liquid sample to be tested in a spectrophotometer, said cell comprising a body member having a cylindrical cavity therein, wherein said cavity has a longitudinal axis in a horizontal plane; wherein said cavity includes bottom and top edges; said cell having first and second ends and opposing end wall members which are optically transparent; said cell further comprising an inlet at said first end which is tangential to said bottom edge of said cavity and an outlet at said second end of said cell which communicates with said top edge.

20. A spectrophotometer system comprising a light source and light detection means; wherein said system comprises a spectrophotometer and a module for holding a sample to be tested; wherein said spectrophotometer includes a receiving port for receiving said module and also includes latch means for locking said module in said receiving port; wherein said module and said spectrophotometer further comprise mating electrical connectors; and wherein said system comprises means for optically aligning said module in said spectrophotometer.

21. A method for optically analyzing a liquid sample, comprising the steps of:
(a) providing a flow cell comprising a body member having a horizontally-disposed cylindrical cavity therein, wherein said cavity includes bottom and top edges; wherein said cell has first and second ends and opposing end wall members which are optically transparent; wherein said cell further comprises an inlet at said first end which is tangential to said bottom edge and an outlet at said second end of said cell which communicates with said top edge; and wherein said inlet is tangential to said cavity;
(b) introducing said liquid sample into said cavity through said inlet;
(c) providing light detection means adjacent one of said end wall members;
(d) directing a light beam through said end wall members of said flow cell toward said light detection means.

* * * * *